(12) United States Patent
Chatelier et al.

(10) Patent No.: US 8,449,740 B2
(45) Date of Patent: May 28, 2013

(54) SYSTEMS AND METHODS FOR DISCRIMINATING CONTROL SOLUTION FROM A PHYSIOLOGICAL SAMPLE

(75) Inventors: Ronald C. Chatelier, Bayswater (AU); Alastair M. Hodges, Blackburn South (AU); Maria Teodorczyk, San Jose, CA (US); Remedios Dato, Pleasanton, CA (US)

(73) Assignee: LifeScan, Inc., Milpitas, CA (US)

( * ) Notice: Subject to any disclaimer, the term of this patent is extended or adjusted under 35 U.S.C. 154(b) by 0 days.

(21) Appl. No.: 12/840,595

(22) Filed: Jul. 21, 2010

(65) Prior Publication Data
US 2011/0011752 A1 Jan. 20, 2011

Related U.S. Application Data

(62) Division of application No. 11/278,333, filed on Mar. 31, 2006.

(51) Int. Cl.
*G01N 27/26* (2006.01)
*G01N 27/327* (2006.01)

(52) U.S. Cl.
USPC ............... 204/403.12; 204/406; 204/403.01; 205/777.5; 205/775; 205/778; 205/792; 600/365; 422/68.1; 702/19

(58) Field of Classification Search
USPC ............... 204/400–403.15, 406; 205/777.5, 205/778, 792, 775; 600/365; 702/19; 422/68.1
See application file for complete search history.

(56) References Cited

U.S. PATENT DOCUMENTS

| | | |
|---|---|---|
| 3,648,160 A | 3/1972 | Beaver |
| 4,088,448 A | 5/1978 | Lilja et al. |
| 4,224,125 A | 9/1980 | Nakamura et al. |
| 4,233,029 A | 11/1980 | Columbus |
| 4,250,257 A | 2/1981 | Lee et al. |
| 4,254,083 A | 3/1981 | Columbus |
| 4,259,165 A | 3/1981 | Miyake |
| 4,301,412 A | 11/1981 | Hill et al. |
| 4,301,414 A | 11/1981 | Hill et al. |

(Continued)

FOREIGN PATENT DOCUMENTS

| | | |
|---|---|---|
| AU | 3104293 A | 7/1993 |
| AU | 5487394 | 8/1994 |

(Continued)

OTHER PUBLICATIONS

U.S. Appl. No. 11/278,333, filed Mar. 31, 2006, R. Chatelier, Sep. 26, 2011 (Notice of Allowance).

(Continued)

*Primary Examiner* — J. Christopher Ball
*Assistant Examiner* — Jennifer Dieterle
(74) *Attorney, Agent, or Firm* — Hiscock & Barclay, LLP

(57) ABSTRACT

Described herein are systems and methods for distinguishing between a control solution and a blood sample. In one aspect, the methods include using a test strip in which multiple current transients are measured by a meter electrically connected to an electrochemical test strip. The current transients are used to determine if a sample is a blood sample or a control solution based on at least two characteristics. Further described herein are methods for calculating a discrimination criteria based upon at least two characteristics. Still further described herein are system for distinguishing between blood samples and control solutions.

4 Claims, 9 Drawing Sheets

U.S. PATENT DOCUMENTS

| | | | |
|---|---|---|---|
| 4,303,887 A | 12/1981 | Hill et al. | |
| 4,307,188 A | 12/1981 | White | |
| 4,374,013 A | 2/1983 | Enfors | |
| 4,404,066 A | 9/1983 | Johnson | |
| 4,431,004 A | 2/1984 | Bessman et al. | |
| 4,436,812 A | 3/1984 | Endoh et al. | |
| 4,508,613 A | 4/1985 | Busta et al. | |
| 4,517,287 A | 5/1985 | Scheibe et al. | |
| 4,517,291 A | 5/1985 | Seago | |
| 4,533,440 A | 8/1985 | Kim | |
| 4,545,382 A | 10/1985 | Higgins et al. | |
| 4,547,735 A | 10/1985 | Kiesewetter | |
| 4,552,840 A | 11/1985 | Riffer | |
| 4,629,563 A | 12/1986 | Wrasidlo | |
| 4,654,197 A | 3/1987 | Lilja et al. | |
| 4,664,119 A | 5/1987 | Bessman et al. | |
| 4,686,479 A | 8/1987 | Young | |
| 4,711,245 A | 12/1987 | Higgins et al. | |
| 4,774,039 A | 9/1988 | Wrasidlo | |
| 4,790,925 A | 12/1988 | Miller et al. | |
| 4,900,424 A | 2/1990 | Birth et al. | |
| 4,919,770 A | 4/1990 | Preidel et al. | |
| 4,963,815 A | 10/1990 | Hafeman | |
| 5,059,908 A | 10/1991 | Mina | |
| 5,064,516 A | 11/1991 | Rupich | |
| 5,089,320 A | 2/1992 | Straus et al. | |
| 5,108,564 A | 4/1992 | Szuminsky et al. | |
| 5,120,420 A | 6/1992 | Nankai et al. | |
| 5,122,244 A | 6/1992 | Hoenes et al. | |
| 5,126,034 A | 6/1992 | Carter et al. | |
| 5,128,015 A | 7/1992 | Szuminsky et al. | |
| 5,141,868 A | 8/1992 | Shanks et al. | |
| 5,151,166 A | 9/1992 | Harral et al. | |
| 5,171,689 A | 12/1992 | Kawaguri et al. | |
| 5,192,415 A | 3/1993 | Yoshioka et al. | |
| 5,229,282 A | 7/1993 | Yoshioka et al. | |
| 5,243,516 A | 9/1993 | White | |
| 5,272,060 A | 12/1993 | Hamamoto et al. | |
| 5,272,087 A | 12/1993 | El Murr et al. | |
| 5,282,950 A | 2/1994 | Dietze et al. | |
| 5,312,590 A | 5/1994 | Gunasingham | |
| 5,320,732 A | 6/1994 | Nankai et al. | |
| 5,352,351 A | 10/1994 | White et al. | |
| 5,382,346 A | 1/1995 | Uenoyama et al. | |
| 5,384,028 A | 1/1995 | Ito | |
| 5,385,846 A | 1/1995 | Kuhn et al. | |
| 5,388,163 A | 2/1995 | Elko et al. | |
| 5,393,399 A | 2/1995 | Van den Berg et al. | |
| 5,395,504 A | 3/1995 | Saurer et al. | |
| 5,405,511 A | 4/1995 | White et al. | |
| 5,413,690 A | 5/1995 | Kost et al. | |
| 5,437,999 A | 8/1995 | Diebold et al. | |
| 5,469,369 A | 11/1995 | Rose-Pehrsson et al. | |
| 5,508,171 A | 4/1996 | Walling et al. | |
| 5,508,203 A | 4/1996 | Fuller | |
| 5,509,410 A | 4/1996 | Hill et al. | |
| 5,520,787 A | 5/1996 | Hanagan et al. | |
| 5,527,446 A | 6/1996 | Kosek et al. | |
| 5,567,302 A | 10/1996 | Song et al. | |
| 5,611,908 A | 3/1997 | Matthiessen et al. | |
| 5,620,579 A | 4/1997 | Genshaw et al. | |
| 5,628,890 A | 5/1997 | Carter et al. | |
| 5,642,734 A | 7/1997 | Ruben | |
| 5,645,709 A | 7/1997 | Birch et al. | |
| 5,653,863 A | 8/1997 | Genshaw et al. | |
| 5,660,791 A | 8/1997 | Brenneman et al. | |
| 5,723,284 A | 3/1998 | Ye | |
| 5,762,770 A | 6/1998 | Pritchard et al. | |
| 5,849,174 A | 12/1998 | Sanghera et al. | |
| 5,869,971 A | 2/1999 | Sherman | |
| 5,909,114 A | 6/1999 | Uchiyama et al. | |
| 5,942,102 A | 8/1999 | Hodges et al. | |
| 5,997,817 A | 12/1999 | Crismore et al. | |
| 6,058,934 A | 5/2000 | Sullivan | |
| 6,071,391 A | 6/2000 | Gotoh et al. | |
| 6,153,069 A | 11/2000 | Pottgen et al. | |
| 6,179,979 B1 | 1/2001 | Hodges et al. | |
| 6,193,873 B1 | 2/2001 | Ohara et al. | |
| 6,251,260 B1 | 6/2001 | Heller et al. | |
| 6,284,125 B1 | 9/2001 | Hodges et al. | |
| 6,287,451 B1 | 9/2001 | Winarta et al. | |
| 6,379,513 B1 | 4/2002 | Chambers et al. | |
| 6,391,645 B1 | 5/2002 | Huang et al. | |
| 6,413,410 B1 | 7/2002 | Hodges et al. | |
| 6,461,496 B1 | 10/2002 | Feldman et al. | |
| 6,475,372 B1 | 11/2002 | Ohara et al. | |
| 6,503,381 B1 | 1/2003 | Gotoh et al. | |
| 6,576,117 B1 | 6/2003 | Iketaki et al. | |
| 6,595,919 B2 | 7/2003 | Berner et al. | |
| 6,645,368 B1 | 11/2003 | Beaty et al. | |
| 6,676,995 B2 | 1/2004 | Dick et al. | |
| 6,730,200 B1 | 5/2004 | Stewart et al. | |
| 6,749,887 B1 | 6/2004 | Dick et al. | |
| 6,816,537 B2 | 11/2004 | Liess | |
| 6,818,180 B2 | 11/2004 | Douglas et al. | |
| 6,824,670 B2 * | 11/2004 | Tokunaga et al. | 205/792 |
| 6,830,934 B1 | 12/2004 | Harding et al. | |
| 6,863,801 B2 | 3/2005 | Hodges et al. | |
| 6,869,411 B2 | 3/2005 | Langley et al. | |
| 6,936,146 B2 | 8/2005 | Ryu et al. | |
| 6,942,770 B2 | 9/2005 | Cai et al. | |
| 7,008,525 B2 | 3/2006 | Morita et al. | |
| 7,018,843 B2 | 3/2006 | Heller | |
| 7,083,712 B2 | 8/2006 | Morita et al. | |
| 7,132,041 B2 | 11/2006 | Deng et al. | |
| 7,201,042 B2 | 4/2007 | Yamaoka et al. | |
| 7,338,639 B2 | 3/2008 | Burke et al. | |
| 7,390,667 B2 | 6/2008 | Burke | |
| 7,407,811 B2 | 8/2008 | Burke | |
| 7,452,457 B2 | 11/2008 | Burke | |
| 7,488,601 B2 | 2/2009 | Burke | |
| 7,494,816 B2 | 2/2009 | Burke | |
| 7,504,020 B2 * | 3/2009 | Tokunaga et al. | 205/792 |
| 7,597,793 B2 | 10/2009 | Burke | |
| 7,604,721 B2 | 10/2009 | Groll | |
| 7,645,373 B2 | 1/2010 | Groll | |
| 7,645,421 B2 | 1/2010 | Groll | |
| 7,718,439 B2 | 5/2010 | Groll | |
| 7,727,467 B2 | 6/2010 | Burke | |
| 7,749,371 B2 | 7/2010 | Guo et al. | |
| 7,749,437 B2 | 7/2010 | Mosoiu | |
| 7,829,023 B2 | 11/2010 | Burke | |
| 7,879,618 B2 | 2/2011 | Mosoiu | |
| 7,892,849 B2 | 2/2011 | Burke | |
| 7,923,258 B2 | 4/2011 | Heller | |
| 7,927,882 B2 | 4/2011 | Heller | |
| 7,955,492 B2 | 6/2011 | Fujiwara | |
| 7,972,861 B2 | 7/2011 | Deng | |
| 7,977,112 B2 | 7/2011 | Burke | |
| 7,981,363 B2 | 7/2011 | Burke | |
| 2002/0139692 A1 | 10/2002 | Tokunaga et al. | |
| 2003/0036202 A1 | 2/2003 | Teodorcyzk et al. | |
| 2003/0098233 A1 | 5/2003 | Kermani et al. | |
| 2003/0109798 A1 | 6/2003 | Kermani | |
| 2004/0005716 A9 | 1/2004 | Beaty | |
| 2004/0079652 A1 | 4/2004 | Vreeke et al. | |
| 2004/0120848 A1 | 6/2004 | Teodorczyk | |
| 2004/0182703 A1 | 9/2004 | Bell et al. | |
| 2004/0219624 A1 | 11/2004 | Teodorcyzk et al. | |
| 2004/0235178 A1 | 11/2004 | Tokunaga et al. | |
| 2004/0256248 A1 | 12/2004 | Burke et al. | |
| 2005/0036906 A1 | 2/2005 | Nakahara | |
| 2005/0153457 A1 | 7/2005 | Patel et al. | |
| 2005/0247562 A1 | 11/2005 | Tokunaga et al. | |
| 2005/0284758 A1 | 12/2005 | Funke | |
| 2006/0108236 A1 | 5/2006 | Kasielke et al. | |
| 2006/0231421 A1 | 10/2006 | Diamond et al. | |
| 2006/0231423 A1 | 10/2006 | Harding et al. | |
| 2006/0231425 A1 | 10/2006 | Harding et al. | |
| 2007/0000777 A1 | 1/2007 | Ho et al. | |
| 2007/0017824 A1 | 1/2007 | Rippeth et al. | |
| 2007/0074977 A1 | 4/2007 | Guo et al. | |
| 2007/0102292 A1 | 5/2007 | Dreibholz et al. | |
| 2007/0227912 A1 | 10/2007 | Chatelier et al. | |
| 2007/0235346 A1 | 10/2007 | Popovich et al. | |
| 2007/0235347 A1 | 10/2007 | Chatelier et al. | |
| 2007/0256943 A1 | 11/2007 | Popovich | |

| | | | |
|---|---|---|---|
| 2008/0083618 A1 | 4/2008 | Neel et al. | |
| 2009/0014339 A1 | 1/2009 | Beer et al. | |
| 2009/0084687 A1 | 4/2009 | Chatelier et al. | |
| 2009/0099787 A1 | 4/2009 | Carpenter | |
| 2009/0184004 A1 | 7/2009 | Chatelier et al. | |
| 2009/0301899 A1 | 12/2009 | Hodges et al. | |
| 2010/0089775 A1 | 4/2010 | Chen | |
| 2010/0170807 A1 | 7/2010 | Diebold | |
| 2010/0206749 A1 | 8/2010 | Choi | |
| 2010/0276303 A1 | 11/2010 | Fujiwara | |
| 2011/0011752 A1 | 1/2011 | Chatelier | |
| 2011/0297554 A1 | 12/2011 | Wu | |
| 2011/0301857 A1 | 12/2011 | Huang | |

FOREIGN PATENT DOCUMENTS

| | | |
|---|---|---|
| AU | 2007201377 | 8/2009 |
| AU | 2009200097 | 1/2011 |
| AU | 2009202200 | 1/2011 |
| CA | 2748433 | 9/2007 |
| CA | 2582643 | 10/2011 |
| DE | 3103464 | 8/1982 |
| EP | 0171375 A1 | 2/1986 |
| EP | 0172969 A2 | 3/1986 |
| EP | 0251915 | 1/1988 |
| EP | 0255291 A1 | 2/1988 |
| EP | 0266204 A2 | 5/1988 |
| EP | 0278647 A2 | 8/1988 |
| EP | 0290770 A2 | 11/1988 |
| EP | 0299779 A2 | 1/1989 |
| EP | 0351516 | 1/1990 |
| EP | 0351891 A2 | 1/1990 |
| EP | 0351892 A2 | 1/1990 |
| EP | 0359831 A1 | 3/1990 |
| EP | 0400918 | 12/1990 |
| EP | 0418404 A1 | 3/1991 |
| EP | 0451981 A2 | 10/1991 |
| EP | 0560336 A1 | 9/1993 |
| EP | 0800086 A1 | 10/1997 |
| EP | 1 042 667 A1 | 10/2000 |
| EP | 1156324 A1 | 11/2001 |
| EP | 1172649 A1 | 1/2002 |
| EP | 1 281 960 * | 7/2002 |
| EP | 1281960 A2 | 2/2003 |
| EP | 1447452 A1 | 8/2004 |
| EP | 1557662 A1 | 7/2005 |
| EP | 1839571 A1 | 10/2007 |
| EP | 1840219 A1 | 10/2007 |
| EP | 2098857 | 12/2009 |
| EP | 2267149 | 12/2010 |
| EP | 2284533 | 2/2011 |
| EP | 2076168 | 1/2012 |
| GB | 2020424 A | 11/1979 |
| GB | 2154735 A | 9/1985 |
| GB | 2201248 A | 8/1988 |
| GB | 2235050 A | 2/1991 |
| JP | 3099254 | 4/1991 |
| JP | 3167464 A | 7/1991 |
| JP | 466112 A | 3/1992 |
| JP | 4343065 A | 11/1992 |
| JP | 5002007 A | 1/1993 |
| JP | 6222874 | 8/1994 |
| JP | 11230934 A | 8/1999 |
| JP | 2001-066274 A | 3/2001 |
| JP | 200166274 | 3/2001 |
| JP | 2001153839 A | 6/2001 |
| JP | 2003114214 A | 4/2003 |
| JP | 2003521708 A | 7/2003 |
| JP | 2003240747 | 8/2003 |
| JP | 2004245836 A | 9/2004 |
| JP | 2005147990 A | 6/2005 |
| JP | 2007087710 | 4/2007 |
| JP | 2007108171 A | 4/2007 |
| JP | 2007133985 | 5/2007 |
| JP | 2007522449 | 8/2007 |
| JP | 2007225619 | 9/2007 |
| JP | 2007248281 | 9/2007 |
| JP | 2007271623 | 10/2007 |
| JP | 2007531877 | 11/2007 |
| JP | 2009528540 | 8/2009 |
| JP | 2009-536744 A | 10/2009 |
| SU | 1351627 | 11/1987 |
| WO | 8908713 A1 | 9/1989 |
| WO | 9215701 A1 | 9/1992 |
| WO | 9402842 A1 | 2/1994 |
| WO | 9516198 A1 | 6/1995 |
| WO | 9700441 A1 | 1/1997 |
| WO | 9718465 A1 | 5/1997 |
| WO | 0020626 A1 | 4/2000 |
| WO | WO 01/40787 * | 6/2001 |
| WO | WO0140787 | 6/2001 |
| WO | 0157510 A2 | 8/2001 |
| WO | 2004040286 A1 | 5/2004 |
| WO | WO 2004/040286 * | 5/2004 |
| WO | WO2004113913 | 12/2004 |
| WO | WO2005066355 | 7/2005 |
| WO | 2005098424 A1 | 10/2005 |
| WO | 2006110504 A1 | 10/2006 |
| WO | WO2006109277 | 4/2007 |
| WO | 2007/133985 A2 | 11/2007 |
| WO | 2007130907 A2 | 11/2007 |
| WO | WO 2008/004565 A1 | 1/2008 |

OTHER PUBLICATIONS

U.S. Appl. No. 12/211,484, filed Sep. 16, 2008, R. Chatelier, Oct. 11, 2011 (Notice of Allowance); Oct. 24, 2011 (Supplemental Notice of Allowance).
U.S. Appl. No. 12/464,935, filed May 13, 2009, L. Rufo, Oct. 12, 2011 (Office Action).
European Search Report, Application No. EP 08253148.4 mailed Nov. 24, 2010.
European Search Report, Application No. EP 10178905, dated Nov. 25, 2010, 7 pages.
Australian Search Report for Australian application No. 2008221593, dated Mar. 29, 2010, 3 pages.
European Search Report, Application No. EP 10178982 mailed Nov. 22, 2010.
Japanese Office Action, Application No. JP 2009-006871 mailed Mar. 1, 2011.
Australian Examiner's Report for application No. 2007201377 dated Mar. 19, 2009, 3 pages.
Canadian Examiner's Requisition for application No. 2582643 dated May 19, 2009, 4 pages.
Canadian Examiner's Requisition for application No. 2582643 dated Mar. 10, 2010, 4 pages.
European Examination Report for application No. 07251388.0 dated Apr. 10, 1008, 4 pages.
Australian Examiner's Report for application No. 2008221593 dated Mar. 30, 3011, 3 pages.
Canadian Examiner's Requisition for application No. 2639776 dated Dec. 21, 2010, 6 pages.
Australian Examiner's Report for application No. 2009200097 dated Jul. 2, 2010, 2 pages.
Australian Examiner's Report for application No. 2011201199 dated May 10, 2011, 2 pages.
European Search Report for application No. 09251507.1 dated May 11, 2011, 5 pages.
Australian Examiner's first report on Patent Application No. 2007201377, dated Jun. 25, 2008.
European Search Report, Application No. EP 09250133, mailed Sep. 15, 2009.
(Abstract Only) Kobayashi Yoshiaki et al., Biosensor, JP 61002060, Jan. 8, 1986., </TD><TR>.
Laszlo Daruhazi et al. "Cyclic Voltammetry for Reversible Redox-Electrode Reactions in Thin-Layer Cells With Closely Separated Working and Auxiliary Electrodes of the Same Size" in J. Electroanal. Chem., 264:77-89 (1989).
Osamu, Niwa, et al., "Electrochemical Behavior of Redox Species at Interdigitated Array Electrodes with Different Geometries: Consideration of Redox Cycling and Collection Efficiency," Analytical Chemistry; Mar. 1990, vol. 62, No. 5, pp. 447-452.
Australian Examiner's first report on Patent Application No. 2009202200, dated Jul. 22, 2010 (3 pages).

Canadian Examiner's Requisition for Application No. 2648625, dated Apr. 11, 2011, 3 pages.
Japanese Office Action for Application No. JP 2007-087710, mailed Aug. 9, 2011, 2 pages.
European Extended Search Report for Application No. EP 09250133, dated Nov. 30, 2009, 10 pages.
European Extended Search Report for Application No. EP 09251507, dated Sep. 14, 2011, 11 pages.
European Extended Search Report for Application No. 07251388.0, dated Jul. 9, 2007, 6 pages.
Chinese Office Action issued Nov. 22, 2011 for Application No. 200910134602.5 (15 Pages).
Japanese Office Action issued Nov. 29, 2011 for Application No. 2009-006871 (3 Pages).
Japanese Office Action issued Jan. 10, 2012 for Application No. 2011-123761 (3 Pages).
Numerical Recipes: The Art of Scientific Computing, Third Edition. William H. Press et al., Cambridge University Press, Published 2007.
EP report for 07251388 dated Jun. 5, 2012.
EP report for 08253148 dated Jun. 4, 2012.
EP report for 10178905 dated Jun. 8, 2012.
EP report for 10178982 dated Jun. 5, 2012.
Wikipedia: Hematocrit; Retrieved on May 24, 2012 (3 pages).
EP report for 12164561 dated Jul. 4, 2012.
Schmidt, "New Principles of amperometric enzyme electrodes . . ." Sensors and Actuators B; vol. 13, No. 1-3, May 1, 1993.
EP report for 12173292 dated Sep. 12, 2012.
EP report for 12173297 dated Sep. 14, 2012.
EP report or 12173284 dated Sep. 7, 2012.
JP report for 2012076986 dated Sepember 4, 2012.
Cha, Kichul, et al., An electronic method for rapid measurement of haematocrit in blood samples; Physio/ Meas, 1994.
CN report for 200910134602 dated Aug. 17, 2012.
JP report or 2009137856 dated Jul. 31, 2012.
EP report for 09251507.1 dated Sep. 13, 2012.
AU report for 2009227823 dated Nov. 1, 2012.
SG report for 200900312-0 dated Oct. 11, 2012.
AU Examination Report for 2012201912; dated Jan. 11 2013; 4 pages.
AU Examination Report for 2012201916; dated Jan. 24, 2013; 4 pages.
AU Examination Report for 2009227823; dated Feb. 18, 2013; 3 pages.
JP Office Action for 2012-261693; dated Feb. 5, 2013; 2 pages.

* cited by examiner

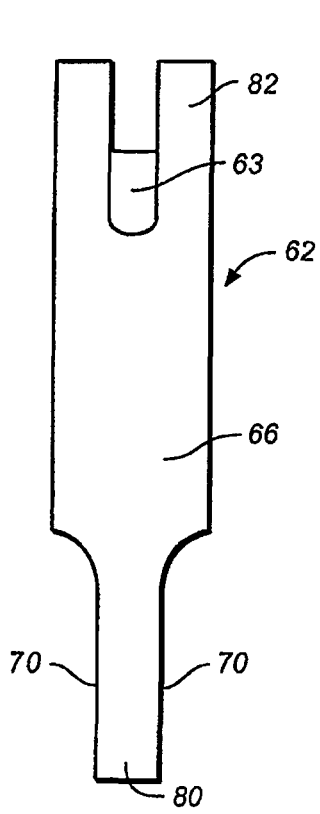 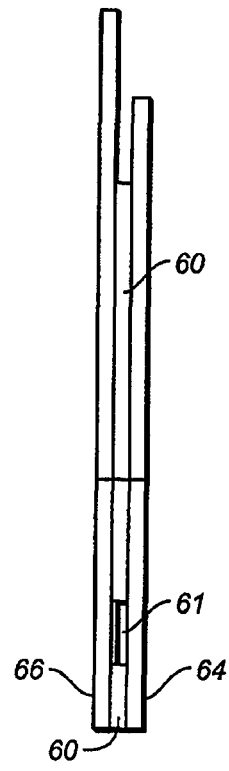 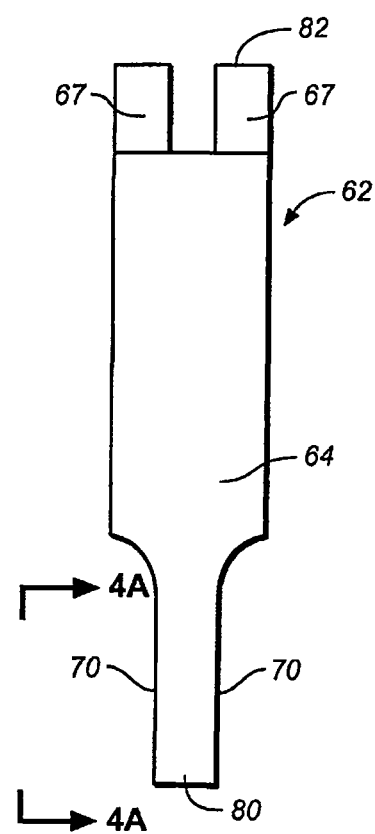
FIG. 2    FIG. 3    FIG. 4A
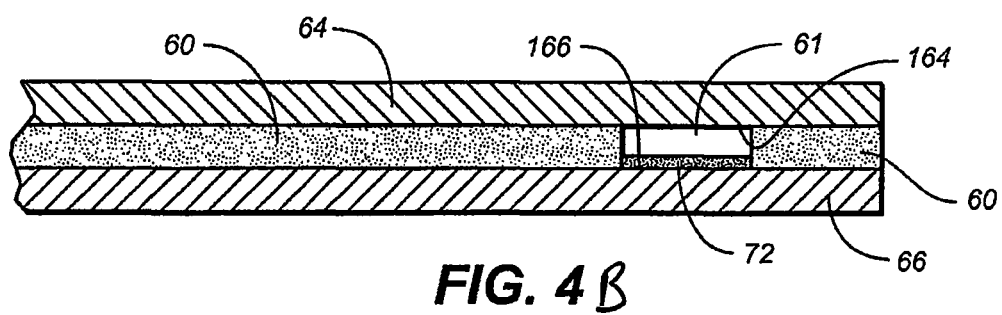
FIG. 4B

_US 8,449,740 B2_

SYSTEMS AND METHODS FOR DISCRIMINATING CONTROL SOLUTION FROM A PHYSIOLOGICAL SAMPLE

CROSS-REFERENCE TO RELATED APPLICATIONS

This application is a divisional of U.S. patent application Ser. No. 11/278,333, filed on Mar. 31, 2006, the contents of which are incorporated herein by reference in their entirety.

BACKGROUND OF THE INVENTION

Analyte concentration determination in physiological fluids (e.g., a test fluid such as blood or blood derived products such as plasma) is of ever increasing importance to today's society. Such assays find use in a variety of applications and settings, including clinical laboratory testing, home testing, etc., where the results of such testing play a prominent role in the diagnosis and management of a variety of disease conditions. Analytes of interest include glucose for diabetes management, cholesterol for monitoring cardiovascular conditions, and the like.

A common method for analyte concentration determination assays is based on electrochemistry. In such methods, an aqueous liquid sample is placed into a sample reaction chamber in an electrochemical cell made up of at least two electrodes, i.e., a reference and working electrode, where the electrodes have an impedance which renders them suitable for amperometric or coulometric measurement. The component to be analyzed is allowed to react directly with an electrode, or directly or indirectly with a reagent to form an oxidizable (or reducible) substance in an amount corresponding to the concentration of the component to be analyzed, i.e., analyte. The quantity of the oxidizable (or reducible) substance present is then estimated electrochemically and related to the amount of analyte present in the initial sample.

An automated device, e.g., an electrochemical test meter is typically employed for determining the concentration of the analyte in the sample. Many test meters advantageously allow for an analyte concentration, and usually a plurality of analyte concentrations, to be stored in the memory of the meter. This feature provides the user with the ability to review analyte concentration levels over a period of time, often times as an average of previously collected analyte levels, where such averaging is performed according to an algorithm associated with the meter. However, to ensure that the system is functioning properly, the user will occasionally perform test using a control fluid instead of blood sample. Such control fluids (also referred to as control solutions) are generally aqueous solutions having a known concentration of glucose. The user can perform a test with the control solution and compare the displayed results with the known concentration to determine if the system is functioning properly. However, once the control solution test is performed, the glucose concentration level of the control fluid is stored in the memory of the meter. Thus, when a user seeks to review previous tests and/or the average concentration of previous test results, the results may be skewed to the concentration of the control fluid analyte level.

Thus, it is desirable to be able to distinguish control solutions and sample fluids during a test. One option is to manually flag the fluids as either control or test fluids. However automatic flagging would be preferable since it minimizes user interaction and increases ease-of-use.

As such, there is continued interest in the development of new methods and devices for use in the determination of analyte concentrations in a sample. Of particular interest would be the development of such methods and devices that include the ability to automatically flag a sample as control fluid or test fluid and to store or exclude measurements accordingly. Of particular interest would be the development of such methods that are suitable for use with electrochemical based analyte concentration determination assays.

SUMMARY

The present invention generally provides systems and methods for distinguishing between a control solution and a blood sample. In one aspect, described herein, are methods of using a test strip in which a potential is applied and a current is measured. Current values are used to determine if a sample is a blood sample or a control solution based on at least one characteristic. Further described herein are methods for calculating a discrimination criteria based upon at least two characteristics. Still further described herein are systems for distinguishing between blood samples and control solutions.

In one embodiment described herein a method for distinguishing between a blood sample and a control solution sample is disclosed. The method includes introducing a sample into an electrochemical cell having first and second electrodes and applying a first test potential between the first electrode and the second electrode. A resulting first current transient is then measured. A second test potential is applied between the first electrode and the second electrode and a second current transient is then measured. The method can also include applying a third test potential between the first electrode and the second electrode, and measuring a third current transient.

Based on the first current transient, a first reference value related to the quantity of redox species in the sample is calculated. In addition, based on the second and third current transients, a second reference value related to reaction kinetics is calculated. The first and second reference values are then used to determine whether the sample is a control sample or a blood sample.

In one aspect, the first reference value is proportional to a concentration of an interferent in the sample. For example, the first reference value can be an interferent index calculated based upon at least one current value from the first current transient. The second reference values can be a function of a percent completion of a chemical reaction. For example, the second reference value can be a residual reaction index calculated based upon at least one current value from the second current transient and at least one current value from the third current transient. In one aspect, the residual reaction index is calculated based upon a ratio of a second current value and a third current value.

In another aspect, the method can perform the step of measuring a concentration of an analyte in the sample. If the sample is found to be a blood sample, the measured concentration can be stored. Conversely, if the sample is found to be a control sample, the measured concentration can be flagged, stored separately, and/or discarded.

In one embodiment, statistical classification can be used to determine if the sample is a control solution or a blood sample. For example, an equation representing an empirically derived discrimination line can be used to evaluate the first and second reference values.

In another aspect, an open-circuit potential is applied to the electrochemical cell before the step of applying the first test potential. In addition, an open-circuit potential can be applied after the step of applying the first test potential.

Further described herein is a system for distinguishing between a blood sample and a control solution sample, the system including a test strip and a test meter. The test strip comprises electrical contacts for mating with the test meter and an electrochemical cell. The test meter includes a processor adapted to receive current data from the test strip, and data storage containing discrimination criteria for distinguishing a blood sample from a control sample based on antioxidant concentration and reaction kinetics. The discrimination criteria can be derived from an interferent index that is representative of antioxidant concentration and a residual reaction index that is representative of reaction kinetics. For example, the discrimination criteria can include an empirically derived discrimination line. The system can further include a control solution that is substantially devoid of redox species.

Still further described herein is a method for calculating a discrimination criterion. The discrimination criterion can be programmed into a test meter for distinguishing between a blood sample and a control solution sample. In one embodiment, the method includes calculating an interferent index and a residual reaction index for a plurality of control solution samples and calculating a discrimination criterion based on a regression of the interferent index and the residual reaction index for the plurality of control solution samples.

In one aspect, the discrimination criterion is a discrimination line. For example, the method can include plotting an interferent index and a residual reaction index for a plurality of blood samples and shifting the discrimination line towards the plurality of blood samples.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 2 is a bottom plan view of the test strip of FIG. 1A;

FIG. 3 is a side plan view of the test strip of FIG. 1A;

FIG. 4A is a top plan view of the test strip of FIG. 1A;

FIG. 4B is an expanded partial side view of the proximal portion of the test strip consistent with arrows 4A-4A of FIG. 4A;

DETAILED DESCRIPTION OF ILLUSTRATIVE EMBODIMENTS OF THE INVENTION

Figure 1A:
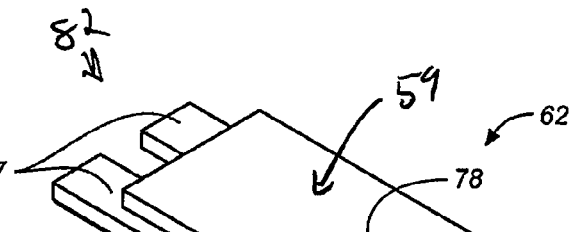
FIG. 1A is a perspective view of an exemplary assembled test strip for use in method described herein.
Figure 1B:
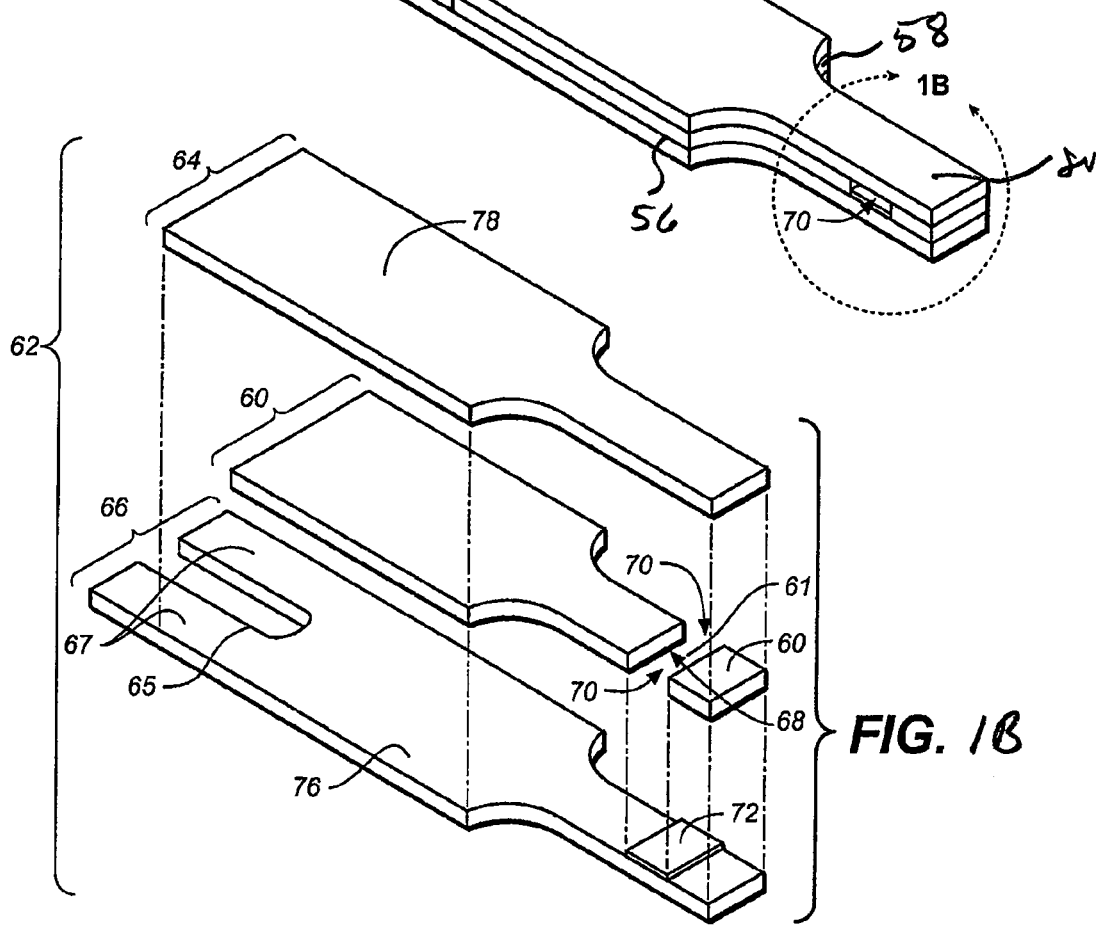
FIG. 1B is an exploded perspective view of the test strip of FIG. 1A.
Figure 1C:
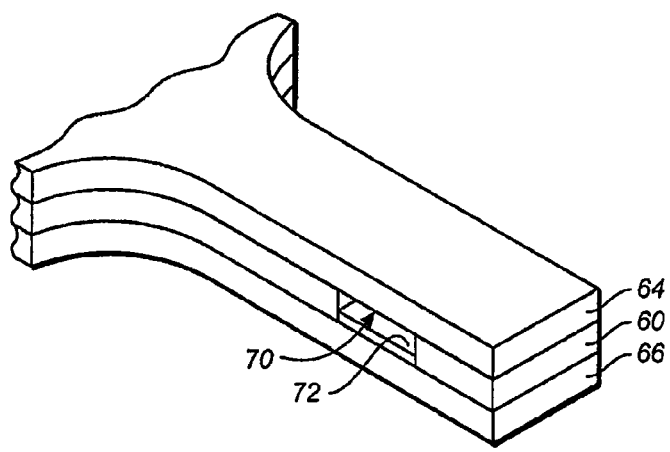
FIG. 1C is an expanded perspective view of a proximal portion of the test strip of FIG. 1A.

The subject systems and methods are suitable for use in the determination of a wide variety of analytes in a wide variety of samples, and are particularly suited for use in the determination of analytes in whole blood or derivatives thereof, where an analyte of particular interest is glucose. In one embodiment, the subject invention provides methods for a test meter to determine whether control solution or blood has been applied to a test strip. In one aspect, at least two characteristics are used to distinguish between a blood sample and a control solution. Described herein are structures of an exemplary test strip embodiment which can be used with the methods and systems disclosed herein. Yet further described herein are methods for calculating a discrimination criterion based upon at least two characteristics. Further, described herein are systems for distinguishing between a blood sample and a control solution.

The subject methods may be used, in principle, with any type of electrochemical cell having spaced apart first and second electrodes and a reagent layer. For example, an electrochemical cell can be in the form of a test strip. In one aspect, the test strip includes two opposing electrodes separated by a thin spacer layer, where these components define a sample reaction chamber or zone in which is located a reagent layer. One skilled in the art will appreciate that other types of test strips, including, for example, test strips with co-planar electrodes could also be used with the methods described herein.

FIGS. 1A to 4B show various views of an exemplary test strip 62 suitable for use with the methods described herein. Test strip 62 can include an elongate body extending from a proximal end 80 to a distal end 82, and having lateral edges 56, 58. The proximal portion of body 59 can include a reaction chamber 61 having electrodes and a reagent, while the distal portion of test strip body 59 can include features adapted for electrically communicating with a test meter. Physiological fluid or control solution can be delivered to reaction chamber 61 and electrochemically analyzed.

In the illustrative embodiment, test strip 62 comprises a first electrode layer 66 and a second electrode layer 64, with a spacer layer 60 positioned therebetween. The first electrode layer 66 can provide a first electrode 166 and a first connection track 76 for electrically connecting the first electrode 166 to a first electrical contact 67. Similarly, second electrode layer 64 can provide a second electrode 164 and a second connection track for electrically connecting the second electrode 164 with a second electrical contact 63.

In one embodiment, sample reaction chamber 61 is defined by first electrode 166, second electrode 164, and spacer 60 as shown in FIGS. 1A to 4B. Specifically, first electrode 166 and second electrode 164 define, respectively, the bottom and top of sample reaction chamber 61. A cutout area 68 of spacer 60 can define the side walls of sample reaction chamber 61. In one aspect, reaction chamber 61 can further include ports 70 that provide a sample inlet and/or a vent. For example, one of the ports can provide a fluid sample ingress and the other port can act as a vent.

Reaction chamber 61 can have a small volume. In one embodiment, the volume ranges from about 0.1 microliters to 5 microliters, preferably about 0.2 microliters to about 3 microliters, and more preferably about 0.3 microliters to about 1 microliter. To provide the small sample volume cutout 68 can have an area ranging from about 0.01 $cm^2$ to about 0.2 $cm^2$, preferably about 0.02 $cm^2$ to about 0.15 $cm^2$, and more preferably about 0.03 $cm^2$ to about 0.08 $cm^2$. In addition, first and second electrode 166, 164 can be spaced in the range of about 1 micron to 500 microns, preferably between about 10 microns and 400 microns, and more preferably between about 40 microns and 200 microns. The close spacing of the electrodes can also allow redox cycling to occur, where oxidized mediator generated at first electrode 166, can diffuse to second electrode 164 to become reduced, and subsequently diffuse back to first electrode 166 to become oxidized again.

At the distal end of test strip body 59, first electrical contact 67 can be used to establish an electrical connection to a test meter. Second electrical contact 63 can be accessed by the test meter through U-shaped notch 65 as illustrated in FIG. 2. One skilled in the art will appreciate that test strip 62 can include a variety of alternative electrical contact configured for electrically connecting to a test meter. For example, U.S. Pat. No. 6,379,513 discloses an electrochemical cell connection means, and is hereby incorporated by reference in its entirety.

In one embodiment, first electrode layer 66 and/or second electrode layer 64 can be a conductive material formed from materials such as gold, palladium, carbon, silver, platinum, tin oxide, iridium, indium, and combinations thereof (e.g., indium doped tin oxide). In addition, the electrodes can be formed by disposing a conductive material onto an insulating sheet (not shown) by a sputtering, electroless plating, or a screen printing process. In one exemplary embodiment, second electrode layer 64 can be a sputtered gold electrode and first electrode layer 66 can be a sputtered palladium electrode. Suitable materials that can be employed as spacing layer 60 include the variety of insulating materials, such as, for example, plastics (e.g., PET, PETG, polyimide, polycarbonate, polystyrene), silicon, ceramic, glass, adhesives, and combinations thereof.

Reagent layer 72 can be disposed within reaction chamber 61 using a process such as slot coating, dispensing from the end of a tube, ink jetting, and screen printing. Such processes are described, for example, in the following U.S. Pat. Nos. 6,749,887; 6,869,411; 6,676,995; and 6,830,934, which are hereby incorporated by reference in their entirety. In one embodiment, reagent layer 72 includes at least a mediator and an enzyme and is deposited onto first electrode 166. Examples of suitable mediators include ferricyanide, ferrocene, ferrocene derivatives, osmium bipyridyl complexes, and quinone derivatives. Examples of suitable enzymes include glucose oxidase, glucose dehydrogenase (GDH) based on pyrroloquinoline quinone (PQQ) co-factor, GDH based on nicotinamide adenine dinucleotide co-factor, and FAD-based GDH [E.C.1.1.99.10]. One exemplary reagent formulation, which would be suitable for making reagent layer 72, is described in pending U.S. application Ser. No. 10/242,951, entitled, Method of Manufacturing a Sterilized and Calibrated Biosensor-Based Medical Device, published as U.S. Published Patent Application No. 2004/0120848, which is hereby incorporated by reference in its entirety.

Either first electrode 166 or second electrode 164 can perform the function of a working electrode which oxidizes or reduces a limiting amount of mediator depending on the polarity of the applied test potential of the test meter. For example, if the current limiting species is a reduced mediator, then it can be oxidized at first electrode 166 as long as a sufficiently positive potential was applied with respect to second electrode 164. In such a situation, first electrode 166 performs the function of the working electrode and second electrode 164 performs the function of a counter/reference electrode. It should be noted that unless otherwise stated for test strip 62, all potentials applied by test meter 100 will hereinafter be stated with respect to second electrode 164.

Similarly, if a sufficiently negative potential is applied with respect to second electrode 164, then the reduced mediator can be oxidized at second electrode 164. In such a situation, second electrode 164 performs the function of the working electrode and first electrode 166 performs the function of the counter/reference electrode.

A first step in the subject methods can include introducing a quantity of the fluid sample of interest into test strip 62 which includes first electrode 166, second electrode 164 and a reagent layer 72. The fluid sample can be whole blood or a derivative or fraction thereof, or control solution. The fluid sample, e.g., blood, is dosed into sample reaction chamber 61 via port 70. In one aspect, port 70 and/or reaction chamber 61 are adapted such that capillary action causes the fluid sample to fill sample reaction chamber 61.

Figure 5:
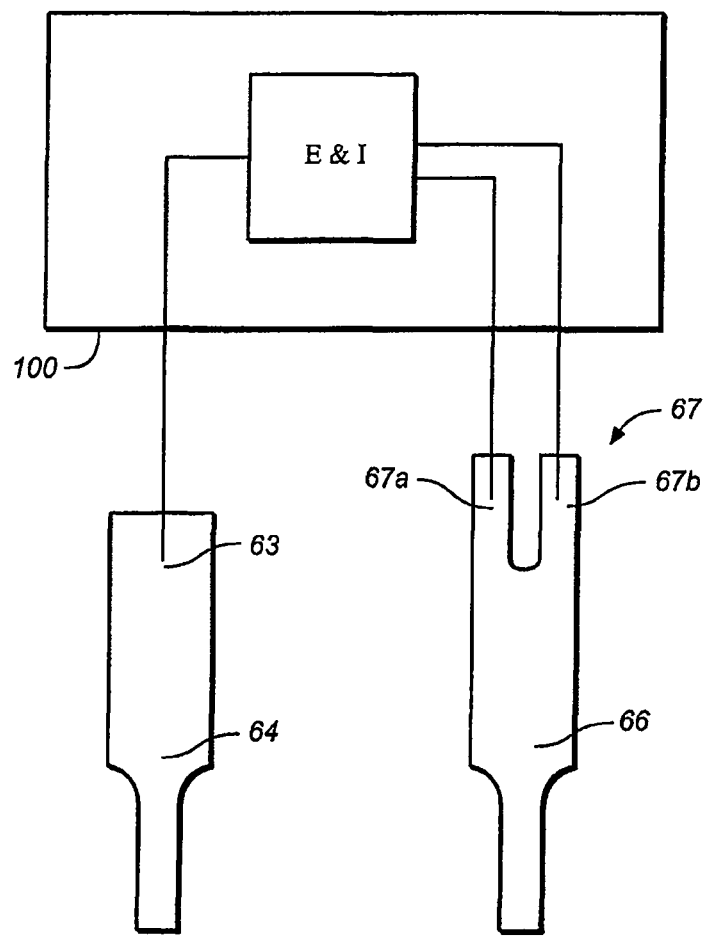
FIG. 5 is a simplified schematic showing a test meter electrically interfacing with portions of the test strip.

FIG. 5 provides a simplified schematic showing a test meter 100 interfacing with first electrical contact 67 and second electrical contact 63, which are in electrical communication with first electrode 166 and second electrode 164, respectively, of test strip 62. Test meter 100 is adapted to electrically connect to first electrode 166 and second electrode 164, via first electrical contact 67 and second electrical contact 63, respectively (as shown in FIGS. 2 and 5). The variety of known test meters can be used with the method described herein. However, in one embodiment the test meter includes at least a processor for performing calculations related to discriminating between blood and a control sample and data storage.

As illustrated in FIG. 5, electrical contact 67 can include two prongs denoted as 67a and 67b. In one exemplary embodiment, test meter 100 separately connects to prongs 67a and 67b, such that when test meter 100 interfaces with test strip 62 a circuit is completed. Test meter 100 can measure the resistance or electrical continuity between prongs 67a and 67b to determine whether test strip 62 is electrically connected to test meter 100. One skilled in the art will appreciate that test meter 100 can use a variety of sensors and circuits to determine when test strip 62 is properly positioned with respect to test meter 100.

In one embodiment, test meter 100 can apply a test potential and/or a current between first electrical contact 67 and second electrical contact 63. Once test meter 100 recognizes that strip 62 has been inserted, test meter 100 turns on and initiates a fluid detection mode. In one embodiment, the fluid detection mode causes test meter 100 to apply a constant current of 1 microampere between first electrode 166 and second electrode 164. Because test strip 62 is initially dry, test meter 100 measures a maximum voltage, which is limited by the hardware within test meter 100. However, once a user doses a fluid sample onto inlet 70, this causes sample reaction chamber 61 to become filled. When the fluid sample bridges the gap between first electrode 166 and second electrode 164, test meter 100 will measure a decrease in measured voltage (e.g., as described in U.S. Pat. No. 6,193,873) which is below a predetermined threshold causing test meter 100 to automatically initiate the glucose test.

It should be noted that the measured voltage may decrease below a pre-determined threshold when only a fraction of sample reaction chamber 61 has been filled. A method of automatically recognizing that a fluid was applied does not necessarily indicate that sample reaction chamber 61 has been completely filled, but can only confirm a presence of some fluid in sample reaction chamber 61. Once test meter 100 determines that a fluid has been applied to test strip 62, a short, but finite amount of time may still be required to allow the fluid to completely fill sample reaction chamber 61.

Figure 6:
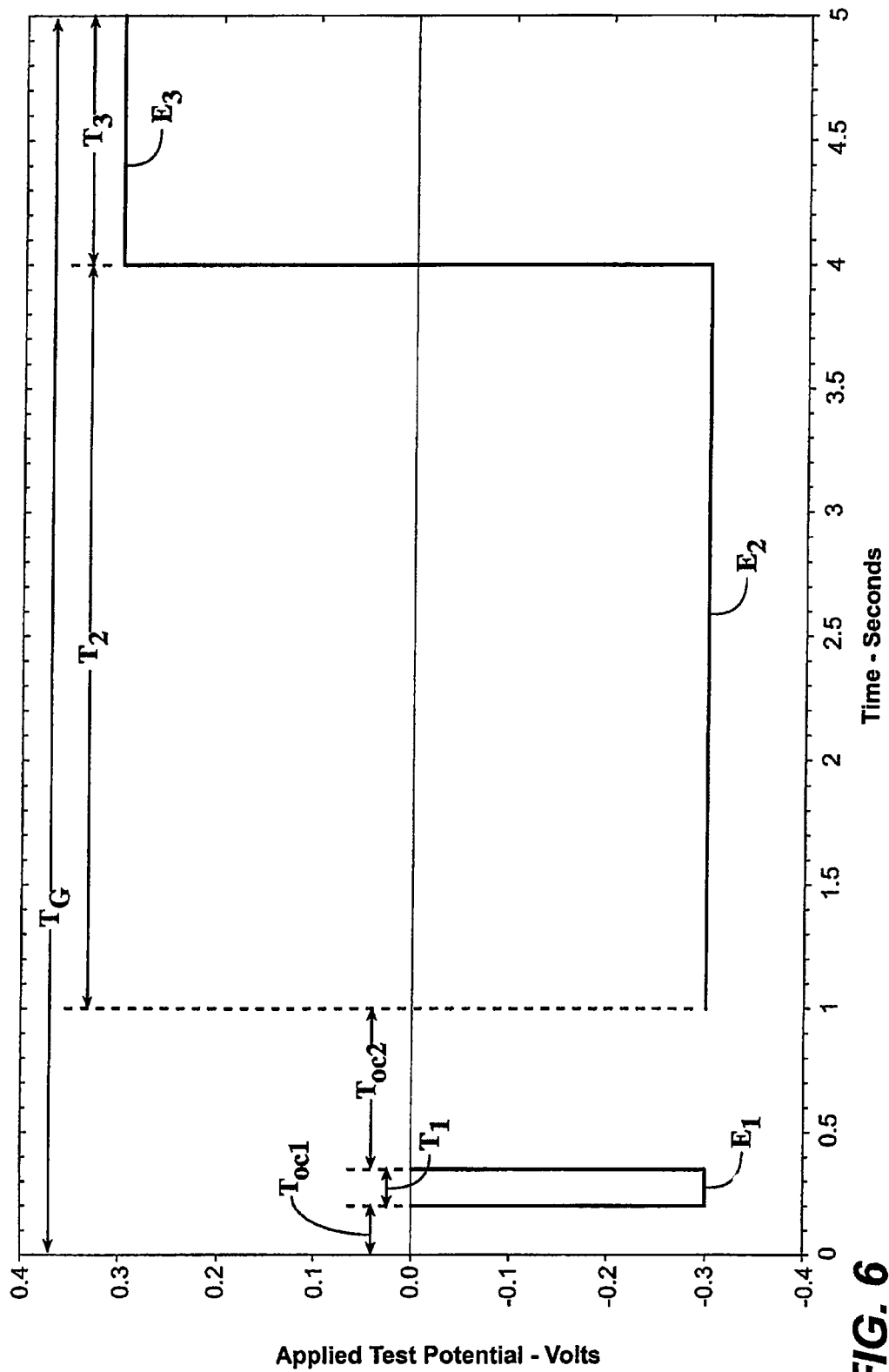
FIG. 6 shows an example of a potential waveform in which the test meter applies a series of open-circuit potentials and test potentials for prescribed time intervals.

In one embodiment, once test meter 100 has determined that a fluid has been dosed onto test strip 62, test meter 100 can perform a glucose test by applying a plurality of open-circuit potentials and a plurality of test potentials to the test strip 62 for prescribed intervals as shown in FIG. 6. A glucose test time interval $T_G$ represents an amount of time to perform the glucose test (but not necessarily all the calculations associated with the glucose test) where glucose test time interval $T_G$ can include a first open-circuit time interval $T_{OC1}$, a first test potential time interval $T_1$, a second open-circuit time interval $T_{OC2}$, a second test potential time interval $T_2$, and a third test potential time interval $T_3$. Glucose test time interval $T_G$ can range from about 1 second to about 5 seconds. While two open-circuit time intervals and three test potential time intervals are described, one skilled in the art will appreciate that the glucose test time interval can comprise different numbers of open-circuit and test potential time intervals. For example, the glucose test time interval could include a single open-circuit time interval and/or only two test potential time intervals.

Once the glucose assay has been initiated, test meter 100 switches to a first open-circuit for a first open-circuit potential time interval $T_{OC1}$, which in the illustrated embodiment is about 0.2 seconds. In another embodiment, first open-circuit time interval $T_{OC1}$ can be in the range of about 0.05 seconds to about 2 seconds and preferably between about 0.1 seconds to about 1.0 seconds, and most preferably between about 0.15 seconds to about 0.6 seconds.

One of the reasons for implementing the first open-circuit is to allow sufficient time for the sample reaction chamber 61 to fill or partially fill with sample. Typically, at ambient temperature (i.e. 22° C.), sample reaction chamber 61 takes about 0.1 seconds to about 0.5 seconds to completely fill with blood. Conversely, at ambient temperature (i.e. 22° C.), sample reaction chamber 61 takes about 0.2 seconds or less to completely fill with control solution, where the control solution is formulated to have a viscosity of about 1 to about 3 centipoise.

While control solutions are composed of known components and are generally uniform, blood samples can vary in their make-up and/or composition. For example, high hematocrit blood samples are more viscous than low hematocrit blood samples, therefore higher hematocrit blood samples require additional time to fill compared with lower hematocrit blood samples. Thus, depending on a variety of factors, blood sample filling time can vary.

Figure 7:
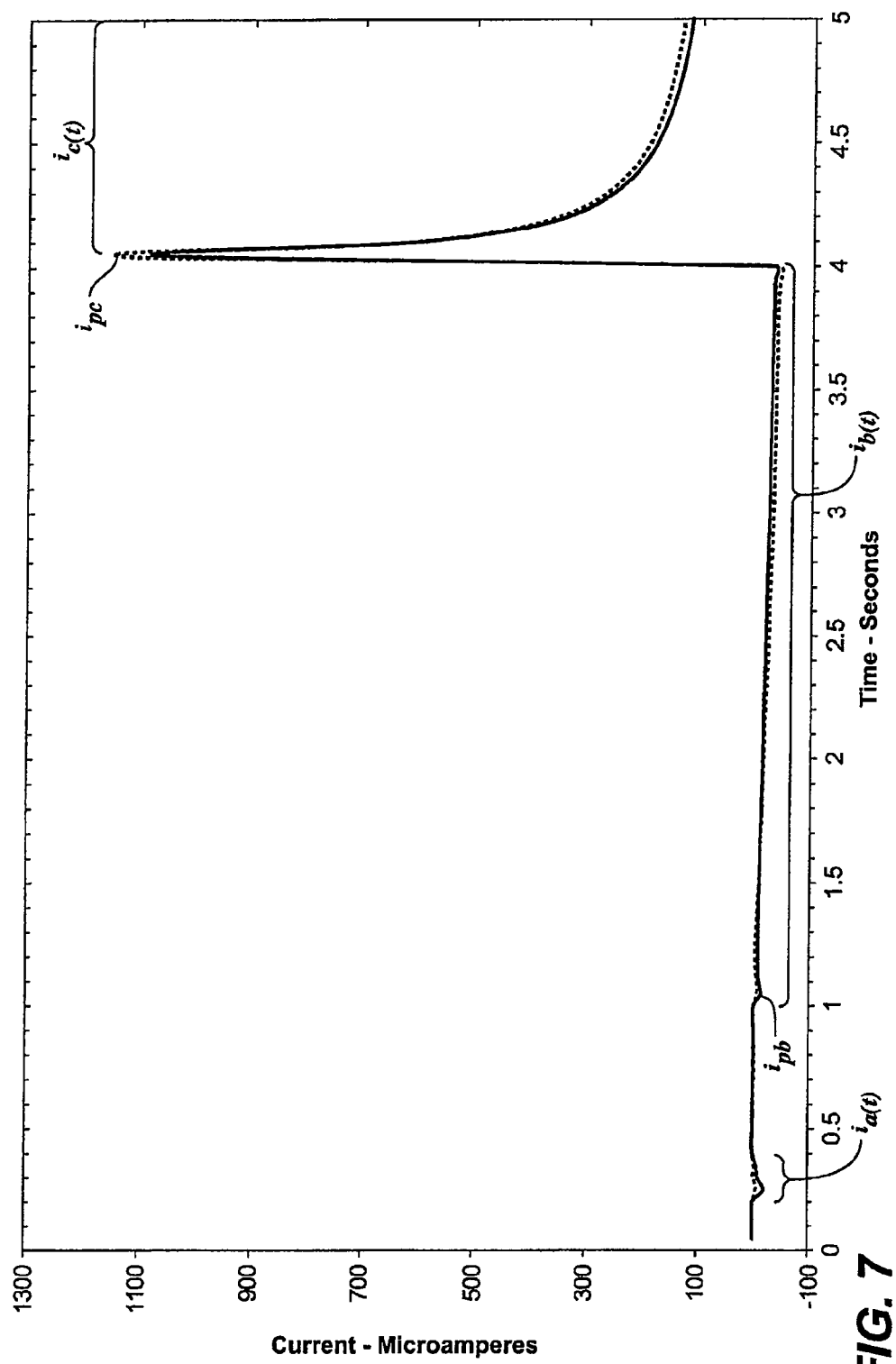
FIG. 7 shows a current transient generated by the test meter that is testing the test strip with the potential waveform of FIG. 6 with a control solution sample (CS, dotted line) and a blood sample (BL, solid line)

After applying the first open-circuit potential, test meter 100 applies a first test potential $E_1$ between first electrode 166 and second electrode 164 (e.g., −0.3 Volts in FIG. 6), for a first test potential time interval $T_1$ (e.g., 0.15 seconds in FIG. 6). Test meter 100 measures the resulting first current transient, which can be referred to as $i_a(1)$ as shown in FIG. 7. In one embodiment, first test potential time interval $T_1$ can be in the range of about 0.05 seconds to about 1.0 second and preferably between about 0.1 seconds to about 0.5 seconds, and most preferably between about 0.1 seconds to about 0.2 seconds.

As discussed below, a portion or all of the first current transient can be used in the methods described herein to determine whether control solution or blood was applied to test strip 62. The magnitude of the first transient current is effected by the presence of easily oxidizable substances in the sample. Blood usually contains endogenous and exogenous compounds that are easily oxidized at second electrode 164. Conversely, control solution can be formulated such that it does not contain oxidizable compounds. However, blood sample composition can vary and the magnitude of the first current transient for high viscosity blood samples will be smaller than low viscosity samples (in some cases even less than control solution samples) because sample reaction chamber 61 may be not be completely filled after 0.2 seconds. An incomplete fill will cause the effective area of first electrode 166 and second electrode 164 to decrease which in turn causes the first current transient to decrease. Thus the presence of oxidizable substances in a sample, by itself, is not always a sufficient discriminatory factor because of variations in blood samples.

After test meter 100 stops applying first test potential $E_1$, it switches to a second open-circuit for a second open-circuit time interval $T_{OC2}$, which in this case is about 0.65 seconds, as shown in FIG. 6. In another embodiment, second open-circuit time interval $T_{OC2}$ can be in the range of about 0.1 seconds to about 2.0 seconds and preferably between about 0.3 seconds to about 1.5 seconds, and most preferably between about 0.5 seconds to about 1.0 seconds.

One of the reasons for implementing the second open-circuit is to provide sufficient time for sample reaction chamber 61 to completely fill, to allow reagent layer 72 to dissolve, and to allow reduced mediator and oxidized mediator to re-equilibrate at the respective first electrode 166 and second electrode 164 from the perturbation caused by first test potential $E_1$. Although sample reaction chamber 61 fills rapidly, second open-circuit time interval $T_{OC2}$ can be sufficiently long to account for conditions which can cause fill times to increase such as low ambient temperature (e.g., about 5° C.) and high hematocrit (e.g., >60% hematocrit).

During first test potential $E_1$, reduced mediator was depleted at second electrode 164 and generated at first electrode 166 to form a concentration gradient. Second open-circuit potential provides time for the reduced mediator concentration profile to become closer to the state immediately before first test potential $E_1$ was applied. As will be described below, a sufficiently long second open-circuit potential is useful because it can allow for glucose concentration to be calculated in the presence of interferents.

An alternative embodiment test potential $E_1'$ can be applied between the electrodes for a duration between when the meter detects that the strip is filling with sample and before a second test potential $E_2$ is applied. In one aspect, test potential $E_1'$ is small. For example, the potential can be between about 1 to 100 mV, preferably between about 5 mV and 50 mV and most preferably between about 10 mV and 30 mV. The smaller potential perturbs the reduced mediator concentration gradient to a lesser extent compared to applying a larger potential difference, but is still sufficient to obtain a measure of the oxidizable substances in the sample. The potential $E_1'$ can be applied for a portion of the time between detection of fill and when $E_2$ is applied or can be applied for the whole of that time period. If $E_1'$ is to be used for a portion of the time then an open-circuit could be applied for the remaining portion of the time. The combination of number of open-circuit and small voltage potential applications, their order and times applied is not critical in this embodiment, as long as the total period for which the small potential $E_1'$ is applied is sufficient to obtain a current measurement indicative of the presence and/or quantity of oxidizable substances present in the sample. In a preferred embodiment the small potential $E_1'$ is applied for the entire period between when fill is detected and when $E_2$ is applied.

Once second open-circuit time interval $T_{OC2}$ or an equivalent time in the small potential $E_1'$ embodiment has elapsed, test meter 100 applies a second test potential $E_2$ between first electrode 166 and second electrode 164 for a second test potential time interval $T_2$. During second test potential time interval $T_2$, test meter 100 can measure a second current transient which may be referred to as $i_b(t)$. After second potential time interval $T_2$ has elapsed, test meter 100 can apply a third test potential $E_3$ between first electrode 166 and second electrode 164 for a third test potential time interval $T_3$, which may be referred to as $i_c(t)$. Second test potential time interval $T_2$ and third test potential time interval $T_3$ can each range from about 0.1 seconds to 4 seconds. For the embodiment shown in FIG. 6, second test potential time interval $T_2$ was 3 seconds and third test potential time interval $T_3$ was 1 second. As mentioned above, in one aspect, an open circuit potential time period can be allowed to elapse between the second test potential $E_2$ and the third test potential $E_3$. Alternatively, the third test potential $E_3$ can be applied immediately following the application of the second test potential $E_2$. Note that a portion of the first, second, or third current transient may be generally referred to as a cell current or a current value.

In one embodiment, first test potential $E_1$ and second test potential $E_2$ both have a first polarity, and that third test potential $E_3$ has a second polarity which is opposite to the first polarity. However, one skilled in the art will appreciate the polarity of the first, second, and third test potentials can be chosen depending on the manner in which analyte concentration is determined and/or depending on the manner in which test samples and control solutions are distinguished.

First test potential $E_1$ and second test potential $E_2$ can be sufficiently negative in magnitude with respect to second electrode 164 such that second electrode 164 functions as a working electrode in which a limiting oxidation current is measured. Conversely, third test potential $E_3$ can be sufficiently positive in magnitude with respect to second electrode 164 such that first electrode 166 functions as a working electrode in which a limiting oxidation current is measured. A limiting oxidation occurs when all oxidizable species have been locally depleted at the working electrode surface such that the measured oxidation current is proportional to the flux of oxidizable species diffusing from the bulk solution towards the working electrode surface. The term bulk solution refers to a portion of the solution sufficiently far away from the working electrode where the oxidizable species was not located within the depletion zone. First test potential $E_1$, second test potential $E_2$, and third test potential $E_3$ can range from about −0.6 Volts to about +0.6 Volts (with respect to second electrode 164) when using either a sputtered gold or palladium working electrode and a ferricyanide mediator.

Figure 8:
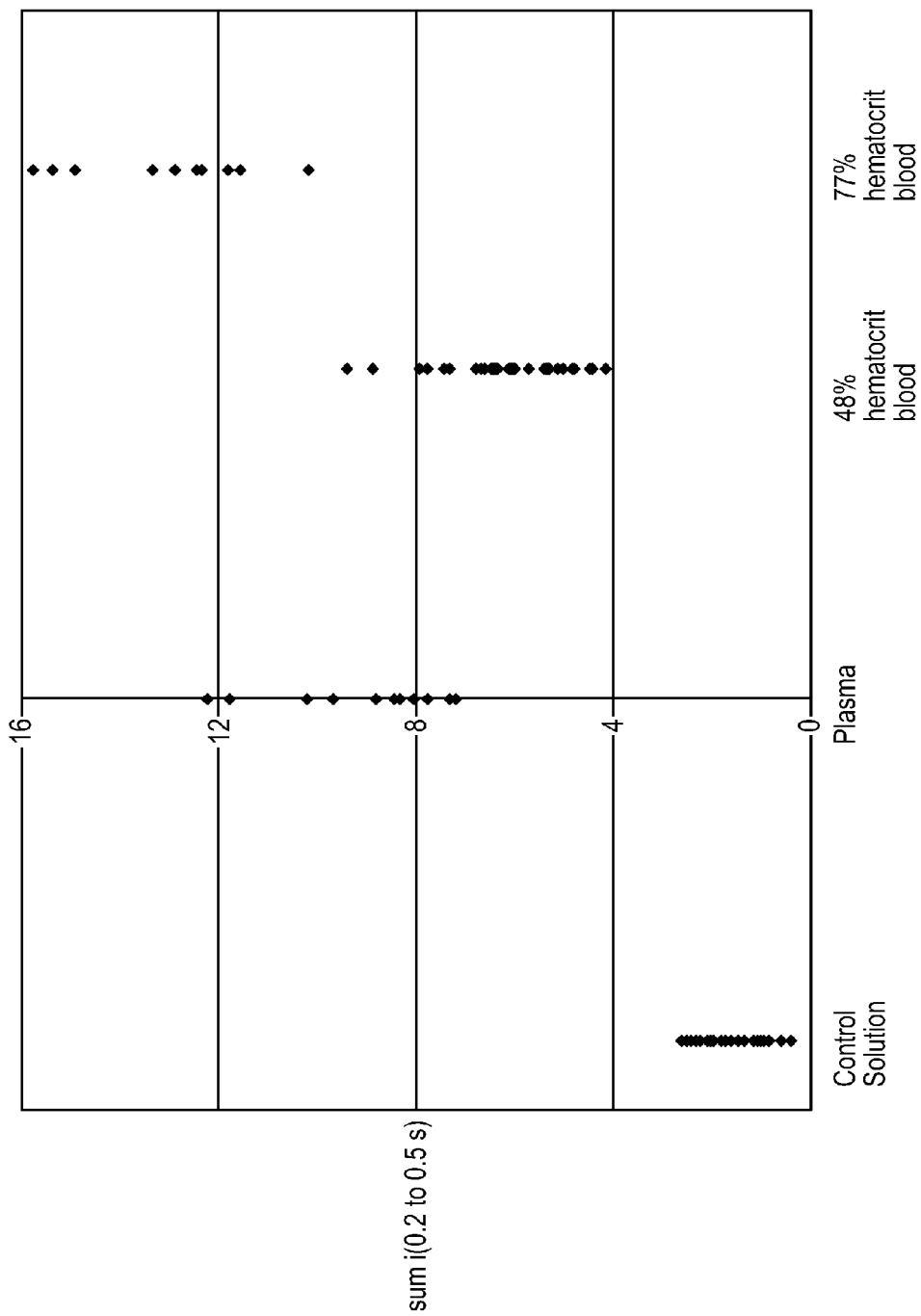
FIG. 8 shows the summation of current values at 0.2 and 0.5 seconds for a control solution, plasma, a blood sample with 48% hematocrit, and a blood sample is 77% when a potential of 20 mV was applied.

FIG. 7 shows a first, second, and third current transients generated by test meter 100 and test strip 62 using either a control solution sample (dotted line) or a blood sample (solid line). The control solution sample contained a 525 mg/dL glucose concentration and the blood sample contained a 530 mg/dL glucose concentration with a 25% hematocrit. FIG. 8 shows an expanded view of first and second current transients in FIG. 7. FIGS. 7 and 8 show the resulting current transients when applying the potential waveform shown in FIG. 6. The description below details how the current transients can be converted into an accurate glucose measurement for the test solution or control solution.

Assuming that a test strip has an opposing face or facing arrangement as shown in FIGS. 1A to 4B, and that a potential waveform is applied to the test strip as shown in FIG. 6, a glucose concentration can be calculated using a glucose algorithm as shown in Equation (Eq.) 1.

$$[G] = \left(\frac{i_2}{i_3}\right)^p \times (a \times i_1 - Z) \qquad \text{Eq. 1}$$

In Eq. 1, [G] is the glucose concentration, $i_1$ is a first current value, $i_2$ is a second current value, and $i_3$ is a third current value, and the terms p, Z, and α are empirically derived calibration constants. A derivation of Eq. 1 can be found in a pending U.S. application Ser. No. 11/240,797 which was filed on Sep. 30, 2005 and entitled "METHOD AND APPARATUS FOR RAPID ELECTROCHEMICAL ANALYSIS", which is hereby incorporated by reference. First current value $i_1$ and second current value $i_2$ are calculated from the third current transient and $i_3$ is calculated from the second current transient. One skilled in the art will appreciate that names "first," "second," and "third" are chosen for convenience and do not necessarily reflect the order in which the current values are calculated. In addition, all current values (e.g., $i_1$, $i_2$, and $i_3$) stated in Eq. 1 use the absolute value of the current.

In another embodiment of this invention, the term $i_1$ can be defined to include peak current values from the second and third current transients to allow for more accurate glucose concentrations in the presence of interferents as shown in Eq. 2.

$$i_1 = i_2 \left\{ \frac{i_{pc} - 2i_{pb} + i_{ss}}{i_{pc} + i_{ss}} \right\} \qquad \text{Eq. 2}$$

The term $i_{pb}$ represents a peak current value for second test potential time interval $T_2$ and the term $i_{pc}$ represents a peak current value for third test potential time interval $T_3$. The term $i_{ss}$ the steady-state current which occurs after the application of third test potential $E_3$. Where Eq. 2 is used, second open-circuit potential time interval $T_{OC2}$ is preferably sufficiently long so as to allow Eq. 2 to compensate for the presence of interferents. When second open-circuit potential time interval $T_{OC2}$ is too short, second peak current value $i_{pb}$ can become distorted and can reduce the effectiveness of the interferent correction calculations. The use of peak current values to account for interferents in a physiological sample are described in an application entitled "Methods and Apparatus for Analyzing a Sample in the Presence of Interferents" (which was filed on the same day as this application, and which is incorporated by reference in its entirety.

In one embodiment of this invention, Eq.'s 1 and 2 can be used together to calculate a glucose concentration for either blood or control solution. In another embodiment of this invention, the algorithm of Eq.'s 1 and 2 can be used for blood with a first set of calibration factors (i.e. α, p, and Z) and a second set of calibration factors can be used for the control solution. When using two different sets of calibration factors, the methods described herein for discriminating between a test fluid and a control solution can improve the effectiveness of the analyte concentration calculations.

In addition, if the test meter determines that the sample type is control solution, the test meter can store the resulting glucose concentration of the control sample such that a user can review test sample concentration data separately from control solution data. For example, the glucose concentrations for control solutions can be stored in a separate database, can be flagged, and/or discarded (i.e., not stored or stored for a short period of time).

Another advantage of being able to recognize control solutions is that a test meter can be programmed to automatically compare the results (e.g., glucose concentration) of the test of the control solution with the expected glucose concentration of the control solution. For example, the test meter can be pre-programmed with the expected glucose level(s) for the control solution(s). Alternatively, a user could input the expected glucose concentration for the control solution. When the test meter recognizes a control solution, the test meter can compare the measured control solution glucose concentration with the expected glucose concentration to determine if the meter is functioning properly. If the measured glucose concentration is out of the expected range, the test meter can output a warning message to alert the user.

In one embodiment, the method described herein uses the presence of redox species to distinguish a control solution from a blood sample. The method can include the step of applying a first test potential $E_1'$ and using one or more current values measured during the test potential as a discriminator. In one aspect, two current values from the first test potential $E_1'$ are summed and used as the discriminator. FIG. 8 shows data for a control solution, plasma, a blood sample with 48% hematocrit, and a blood sample is 77% hematocrit. A potential of 20 mV was applied for the first 1 second and current values at 0.2 to 0.5 seconds were summed. As show in FIG. 8, the summed current values were sufficient to distinguish between a control solution (that was substantially devoid of interferents) and blood samples.

In another embodiment, two characteristics of control solution are used to distinguish control solutions from blood—the presence and/or concentration of redox species in the sample and reaction kinetics. The method disclosed herein can include the step of calculating a first reference value that is representative of the redox concentration in the sample and a second reference value that is representative of the rate of reaction of the sample with the reagent. In one embodiment, the first reference value is an interferent oxidation current and the second reference value is a reaction completion percentage.

In regard to redox species in the sample, blood usually contains various endogenous redox species or "interferents" such as ascorbic acid and uric acid, as well as exogenously derived interferents such as gentisic acid (gentisic acid is a metabolite of aspirin). Endogenous interferents are chemical species that can be easily oxidized at an electrode and are usually present in blood within a physiological range for healthy individuals. Exogenously derived interferents are also a chemical species that can be easily oxidized at an electrode, but are not usually present in blood unless they are inputted into the body via consumption, injection, absorption, and the like.

Figure 9:
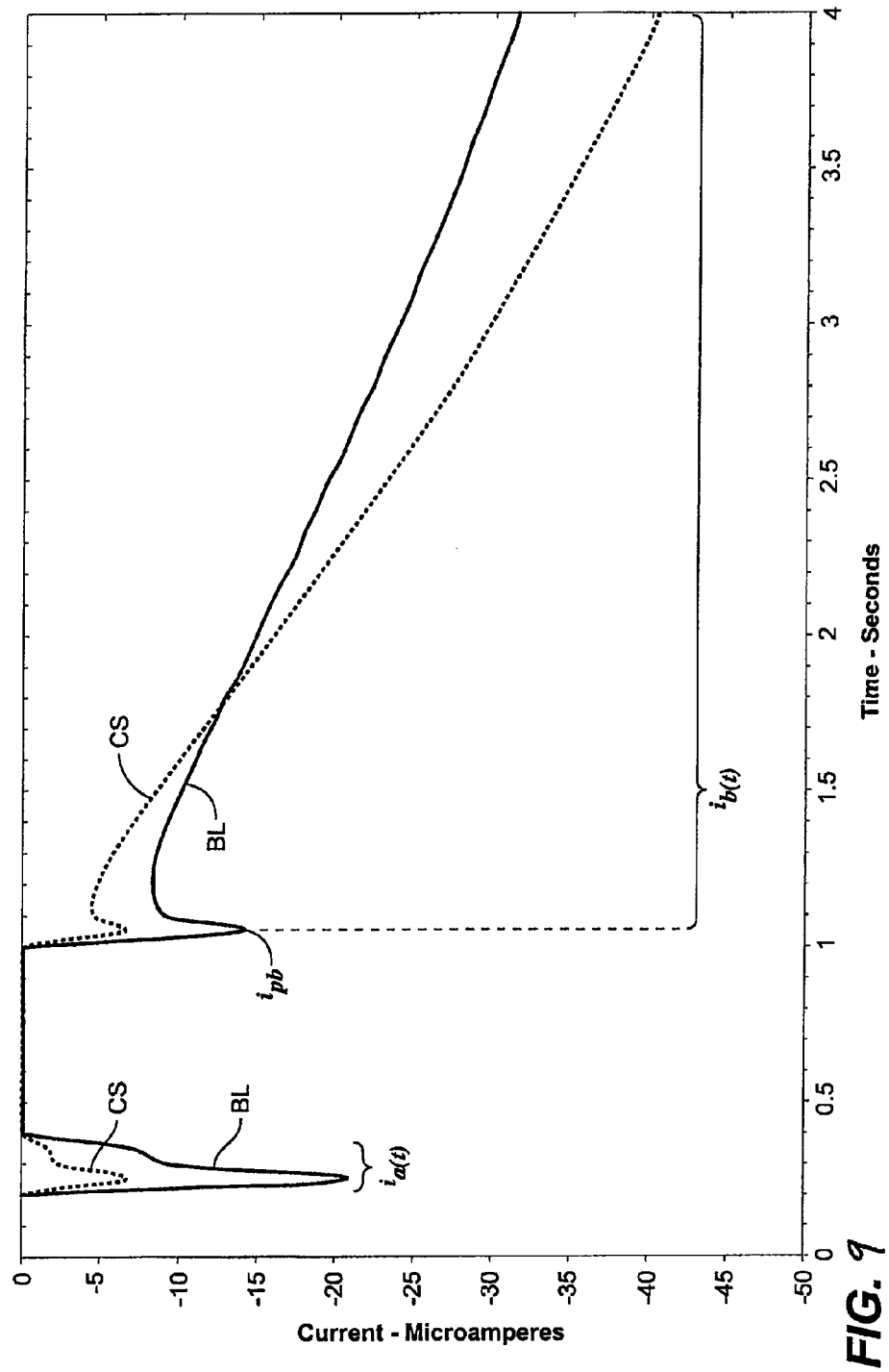
FIG. 9 is an expanded view of FIG. 7 showing a first test current transient and second test current transient for control solution (CS) and blood (BL)

Control solution can be formulated to be either essentially free of antioxidants or to have a relatively high interferent concentration compared to the interferent concentration in a blood sample. For the case in which control solution is essentially free of antioxidants, the magnitude of the first current transient should be smaller for control solution than for a blood sample as shown in FIG. 9. For the case in which control solution has a relatively high concentration of interferents, the magnitude of the first current transient should be larger for control solution than for a blood sample (data not shown).

An interferent index can be calculated based on the current values within first current transient. In one embodiment, the interferent index can include a summation of current values at two points in time during the first current transient. In one example, the current values at 0.3 and 0.35 seconds can be used. In another embodiment when a small potential $E_1'$ is applied for the entire period between when fill is detected and $E_2$, the interferent index is preferably obtained by summing two values over a longer period, for example 0.2 seconds to 0.5 seconds.

In general, the interferent index will be proportional to the interferent concentration and should not substantially depend on the glucose concentration. Therefore, in theory, the test meter should be able to distinguish whether the sample is blood or control solution based on the interferent index. However, in practice, using only the interferent index did not always sufficiently discriminate between blood and control solution. Although blood typically has a much higher interferent concentration, there are certain conditions in which the first current transient for blood may be attenuated such that it is comparable to control solution. These conditions include high glucose concentration, high hematocrit, low temperature, and incomplete filling of sample reaction chamber 61. Thus, in one embodiment, an additional factor was implemented to enable the test meter to sufficiently discriminate between blood and control solution.

The additional factor used for helping discriminate between blood and control solution can be a residual reaction index which is a function of the percent of remaining substrate which would have reacted if given enough time. The residual reaction index relates to the reaction rate in that a high reaction rate can cause the substrate to be depleted by the reaction. However, the residual reaction index will also depend on the initial magnitude of the substrate concentration.

Reagent layer 72 can include glucose dehydrogenase (GDH) based on the PQQ co-factor and ferricyanide. When blood or control solution is dosed into sample reaction chamber 61, glucose is oxidized by $GDH_{(ox)}$ and in the process converts $GDH_{(ox)}$ to $GDH_{(red)}$, as shown in Eq.3. Note that $GDH_{(ox)}$ refers to the oxidized state of GDH, and $GDH_{(red)}$ refers to the reduced state of GDH.

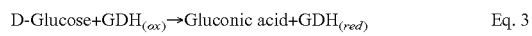

$$\text{D-Glucose} + GDH_{(ox)} \rightarrow \text{Gluconic acid} + GDH_{(red)} \qquad \text{Eq. 3}$$

Next, $GDH_{(red)}$ is regenerated back to its active oxidized state by ferricyanide (i.e. oxidized mediator or $Fe(CN)_6^{3-}$) as shown in Eq. 4. In the process of regenerating $GDH_{ox}$, ferrocyanide (i.e. reduced mediator or $Fe(CN)_6^{4-}$) is generated from the reaction as shown in Eq. 4.

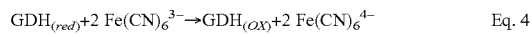

$$GDH_{(red)} + 2\,Fe(CN)_6^{3-} \rightarrow GDH_{(OX)} + 2\,Fe(CN)_6^{4-} \qquad \text{Eq. 4}$$

In general, the rate of glucose consumption based on Eq.'s 3 and 4 is faster for control solution than blood. Typically, control solution is less viscous than blood causing the reaction rate of Eq. 3 and 4 to be faster for control solution. Further, the reaction rate is faster for control solution because a portion of the glucose present in the blood sample must diffuse out of the red blood cells to participate in Eq. 3. This extra step of glucose diffusion out of the red blood cells slows down the reaction rate to some measurable degree. FIG. 9 shows that the reaction rate for blood is slower than for control solution as evidenced by the fact that the general absolute slope value (e.g., between 1.2 and 4 seconds) for the second current transient is less for the blood sample. Because of the faster reaction rates in control solution compared to blood, the residual reaction index for control solution will generally be lower than for blood.

The residual reaction index is a number which is related to the percent of glucose which has not been consumed. A relatively low residual reaction index will indicate that the reactions of Eq.'s 3 and 4 are close to completion. In contrast, a relatively high residual reaction index will indicate that the reaction is not close to completion. In one embodiment, the residual reaction index can be an absolute ratio of a current value of third current transient divided by a current value of the second current transient, as shown in Eq. 5.

$$\text{abs}\left(\frac{i(4.15)}{i(3.8)}\right) \qquad \text{Eq. 5}$$

For the denominator of Eq. 5, the current value at 3.8 seconds for the second current transient is used. The time of 3.8 seconds was chosen empirically, however, one skilled in the art will appreciate that other current values can be used. In one embodiment, a current value towards the end of the second current transient is chosen. During the second current transient time interval $T_2$, reduced mediator is oxidized at second electrode 164. The current values measured during second current transient time interval $T_2$ were ascribed to ferrocyanide generated by reagent layer 72 at first electrode 166 which then diffused to second electrode 164 and became oxidized. It is assumed that reagent layer 72 remains close to first electrode 166 after it dissolves in blood causing most of the ferrocyanide generated by reagent layer 72 to also be close to first electrode 166. A portion of this generated ferrocyanide can diffuse to second electrode 164.

For the numerator of Eq. 5, the current value at 4.15 seconds was used. Other current values from the third current transient can be chosen, however current value towards the beginning of the third current transient are preferred. During the third current transient time interval $T_3$, reduced mediator is oxidized at first electrode 166. The current values measured during second current transient time interval $T_2$ were ascribed to ferrocyanide generated by reagent layer 72 at first electrode 166. Therefore, the current values for the third current transient will be larger than the second current transient because most of the ferrocyanide will be close to first electrode 166 because first electrode 166 was coated with reagent layer 72. In addition, third current transient will also be larger than second current transient because it occurs later in the glucose test allowing for more ferrocyanide to be generated. Thus, the absolute ratio as shown in Eq. 5 will be larger if the glucose reaction is still far from completion at the time of the measurement.

Figure 10:
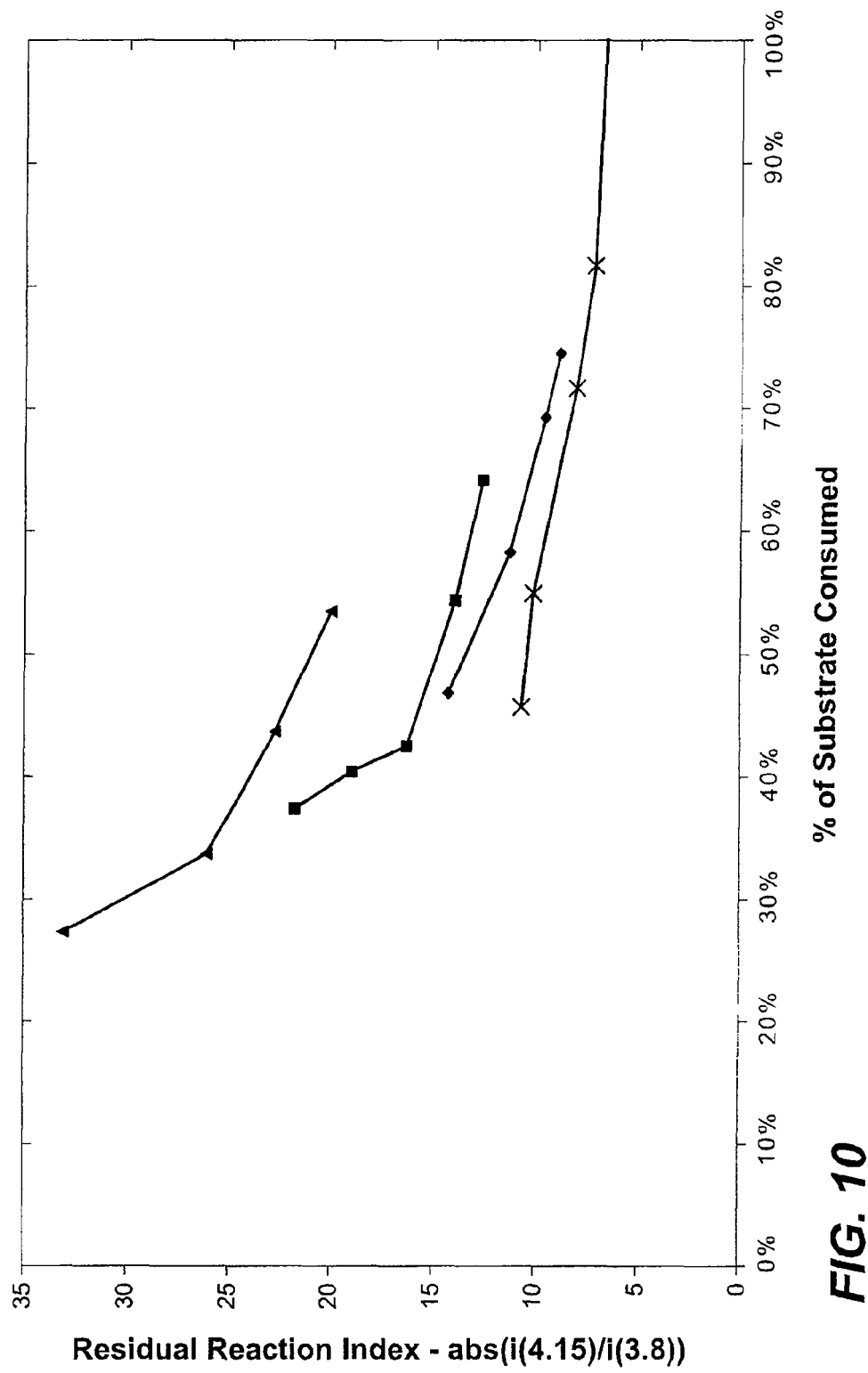
FIG. 10 is a chart showing a non-linear relationship between the % of substrate consumed and the residual reaction index for blood samples having various hematocrit levels and for control solution (diamonds=25% hematocrit blood, squares=42% blood, triangles=60% hematocrit blood, x=control solution.

FIG. 10 is a chart showing a non-linear relationship between the % of substrate consumed and the residual reaction index for blood samples having various hematocrit levels and for control solution (diamonds=25% hematocrit blood, squares=42% blood, triangles=60% hematocrit blood, x=control solution). This chart shows that the residual reaction index is relatively high when the % of substrate consumed is low and that the residual reaction index is relatively low when the % of substrate consumed is high for a given sample type/hematocrit value. The % of substrate consumed is derived from a ratio $$\frac{C_o}{YSI},$$

where $C_o$ is the substrate concentration at the electrode surface and YSI is the substrate concentration using a standard reference technique. The term $C_o$ is derived using the following Eq. 6, $$C_o = \frac{i_{ss}L}{2FAD} \qquad \text{Eq. 6}$$

where L is the distance between first electrode 166 and second electrode 164, F is Faraday's constant, A is the area of first electrode 166, and D is the diffusion coefficient.

Figure 11:
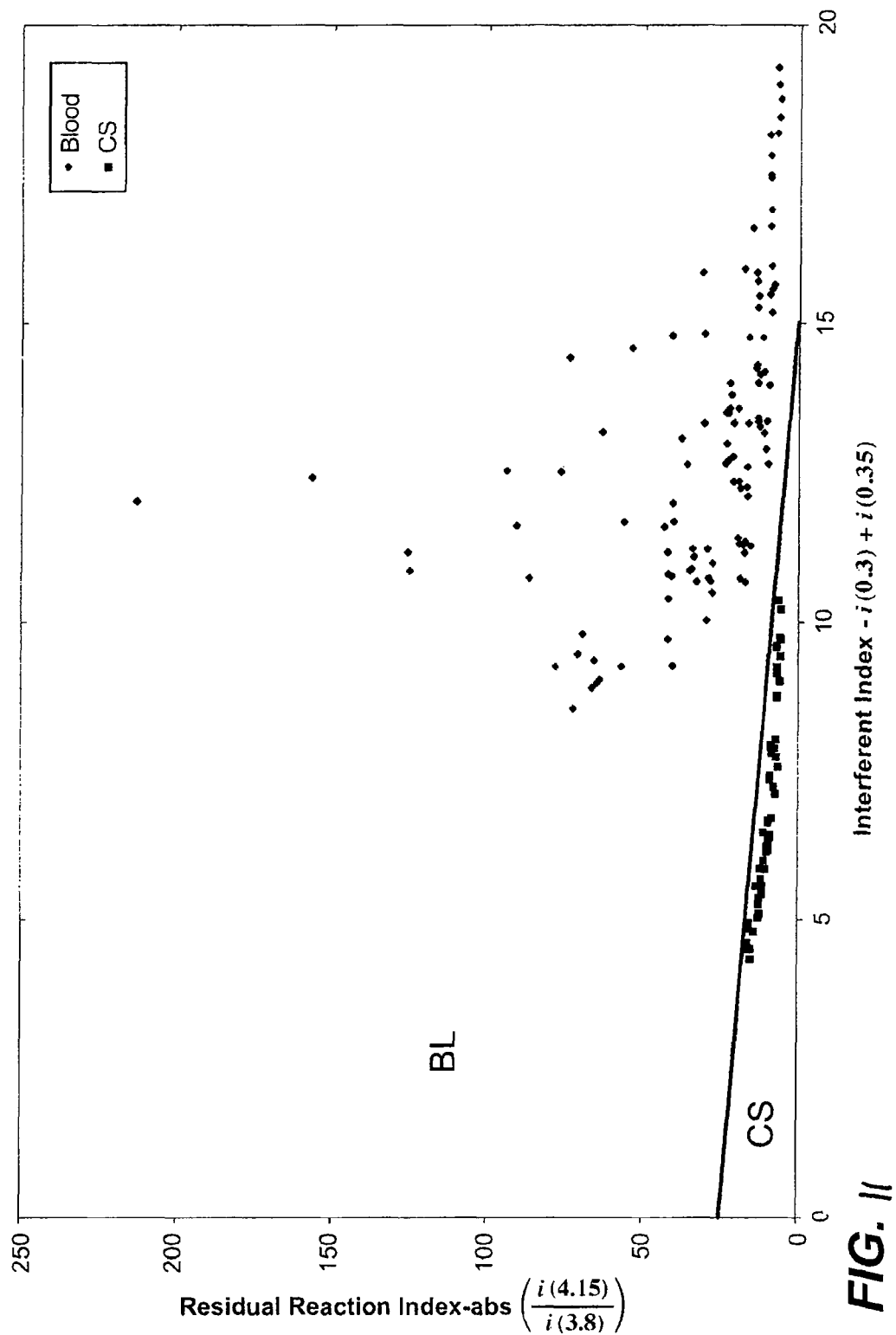
FIG. 11 is a chart showing a relationship between an interferent index and a residual reaction index for a plurality of blood samples (diamonds) and control solution samples (squares).

FIG. 11 is a chart showing a relationship between an interferent index and a residual reaction index for a plurality of blood samples and control solution samples. By plotting the interferent index on the X-axis and the residual reaction index on the Y-axis, a segregation between blood and control solution can be observed. A discrimination line can be drawn to determine if the sample is either control solution or blood. In this embodiment, the interferent index is $i(0.3)+i(0.35)$ and the residual reaction index is abs $$\text{abs}\left(\frac{i(4.15)}{i(3.8)}\right).$$

It should be noted that the times (e.g., 4.15, 3.8) at which the current values where selected for the residual reaction index, were found empirically. A large number of current ratios were evaluated for their ability to discriminate between blood and control solution samples. The ratio shown in Eq. 5 was selected because it was found to produce significant separation between blood and control solution samples.

A discrimination line was derived to allow the test meter to determine whether the sample was control solution or blood. For all of the control solution samples tested, the interferent index was plotted versus the residual reaction index. Next, a line was calculated using linear regression for control solution samples. After calculating an equation for the line, the perpendicular bias between each data point and the line was calculated. The perpendicular bias represents the shortest distance between the data point and the line as opposed to a vertical bias which is commonly calculated. A standard deviation was determined for all of the perpendicular biases ($SD_{perp}$). Lastly, the line is shifted $3*SD_{perp}$ units towards the data points for the blood group. The reason for this approach is that the data for the control solution group show very little scatter and therefore the "99% confidence limit" of the control solution group is well-defined.

In the method described herein, the information obtained from this statistical analysis of the residual reaction index and the interferent index can be used by the test meter to distinguish control solutions from blood samples. The test meter can calculate the interferent index and residual reaction index and use these values in association with the derived discrimination line (or an equation representing the discrimination line) to distinguish control solutions from blood samples.

EXAMPLE 1

Preparation of control fluid is disclosed below. The prepared control fluid was used in the experiments which produced the data illustrated in FIGS. 7 and 11.

Citraconic acid Buffer Component 0.0833 g
Dipotassium citraconate Buffer Component 1.931 g
Methyl Paraben Preservative 0.050 g
Germal II Preservative 0.400 g
Dextran T-500 Viscosity Modifier 3.000 g
Pluronic 25R2 Wicking Agent 0.050 g
1-[(6-methoxy-4-sulfo-m-tolyl)azo]-2-naphthol-6-sulfonic acid disodium salt Dye (FD&C Blue No. 1) 0.100 g
D-Glucose Analyte 50, 120, or 525 mg
Deionized Water Solvent 100 g First citraconic buffer pH 6.5±0.1 was prepared by dissolving required quantities of citraconic acid and dipotassium citraconate in deionized water. Next, Methyl Paraben was added and the solution was stirred until the preservative was fully dissolved. Subsequently Dextran T-500, Germal II, Pluronic 25R2 and 1-[(6-methoxy-4-sulfo-m-tolyl)azo]-2-naphthol-6-sulfonic acid disodium salt were added sequentially, following complete dissolution of the previously added chemical. At this point, the pH of the control fluid was verified, followed by addition of the requisite quantity of glucose to obtain a low, normal or high glucose level of control fluid. After the glucose was dissolved completely, the control fluid was left at room temperature overnight. Finally, the glucose concentration was verified using a Model 2700 Select Biochemistry Analyzer manufactured by Yellow Springs Instrument Co., Inc. The dye used in this control solution has a blue color which reduces the possibility of a user confusing control solution with blood, which is normally red.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A system for distinguishing between a blood sample and a control solution sample, the system comprising:
  A. a test strip including electrical contacts for mating with a test meter and an electrochemical cell, said cell comprising
    (i) a first electrode and a second electrode in a spaced apart relationship, and
    (ii) a reagent, and;
  B. a test meter including a processor programmed to receive respective first, second and third current transients resulting from respective first, second and third electrical potentials applied to the test strip in which the third electrical potential is opposite in polarity to the first and second potentials, calculates a residual reaction index based on a ratio of the third current to the second current transients and an interferent index, and compares both the residual reaction index and the interferent index with data storage containing discrimination criteria relating to both the residual reaction index and the interferent index to distinguish a blood sample from a control solution sample based on the discrimination criteria.

2. The system of claim 1, further comprising a control solution sample that is substantially devoid of redox species.

3. The system of claim 1, wherein the discrimination criteria is derived from an interferent index that is representative of antioxidant concentration and a residual reaction index that is representative of the percentage of the analyte that is unconsumed.

4. The system of claim 3, wherein the discrimination criteria includes an empirically derived discrimination line.

* * * * *